United States Patent
Zyhowski et al.

(10) Patent No.: US 8,820,079 B2
(45) Date of Patent: Sep. 2, 2014

(54) CHLORO- AND BROMO-FLUORO OLEFIN COMPOUNDS USEFUL AS ORGANIC RANKINE CYCLE WORKING FLUIDS

(75) Inventors: Gary Zyhowski, Lancaster, NY (US); Ryan J. Hulse, Getzville, NY (US); Haridasan K. Nair, Williamsville, NY (US); David Nalewajek, West Seneca, NY (US); Rajiv R. Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 889 days.

(21) Appl. No.: 12/630,647

(22) Filed: Dec. 3, 2009

(65) Prior Publication Data

US 2010/0139274 A1  Jun. 10, 2010

Related U.S. Application Data

(63) Continuation-in-part of application No. 12/351,807, filed on Jan. 9, 2009.

(60) Provisional application No. 61/120,125, filed on Dec. 5, 2008.

(51) Int. Cl.
*F01K 25/08* (2006.01)
*C09K 5/04* (2006.01)
*F25B 25/00* (2006.01)

(52) U.S. Cl.
USPC ............... 60/651; 60/655; 60/671; 62/112; 62/114; 252/68

(58) Field of Classification Search
USPC ............. 60/651, 655, 671; 62/112, 114, 115; 252/67, 68
See application file for complete search history.

(56) References Cited

U.S. PATENT DOCUMENTS

| 5,611,210 A | 3/1997 | Nimitz et al. |
| 5,674,451 A | 10/1997 | Nimitz et al. |

(Continued)

FOREIGN PATENT DOCUMENTS

| JP | 04-110388 A | 4/1992 |
| WO | 2006069362 A2 | 6/2006 |

(Continued)

OTHER PUBLICATIONS

EP Supplementary Search Report, EP 09831221, dated Jun. 29, 2011.

(Continued)

*Primary Examiner* — Hoang Nguyen
(74) *Attorney, Agent, or Firm* — Colleen D. Szuch

(57) ABSTRACT

Aspects of the present invention are directed to working fluids and their use in processes wherein the working fluids comprise compounds having the structure of formula (I):

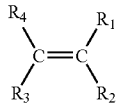

wherein $R_1$, $R_2$, $R_3$, and $R_4$ are each independently selected from the group consisting of: H, F, Cl, Br, and $C_1$-$C_6$ alkyl, at least $C_6$ aryl, at least $C_3$ cycloalkyl, and $C_6$-$C_{15}$ alkylaryl optionally substituted with at least one F, Cl, or Br, wherein formula (I) contains at least one F and at least one Cl or Br, provided that if any R is Br, then the compound does not have hydrogen. The working fluids are useful in Rankine cycle systems for efficiently converting waste heat generated from industrial processes, such as electric power generation from fuel cells, into mechanical energy or further to electric power. The working fluids of the invention are also useful in equipment employing other thermal energy conversion processes and cycles.

19 Claims, 1 Drawing Sheet

(56) References Cited

U.S. PATENT DOCUMENTS

| | | |
|---|---|---|
| 5,710,352 A | 1/1998 | Tung |
| 5,744,052 A | 4/1998 | Bivens |
| 5,800,730 A | 9/1998 | Bivens et al. |
| 6,076,355 A | 6/2000 | Ven et al. |
| 6,176,102 B1 | 1/2001 | Novak et al. |
| 6,374,629 B1 | 4/2002 | Oberle et al. |
| 6,551,469 B1 * | 4/2003 | Nair et al. ............ 204/157.95 |
| 6,640,841 B2 | 11/2003 | Thomas et al. |
| 6,783,691 B1 | 8/2004 | Bivens et al. |
| 6,844,475 B1 * | 1/2005 | Tung et al. ................. 570/168 |
| 6,858,571 B2 | 2/2005 | Pham et al. |
| 6,991,744 B2 | 1/2006 | Mahler et al. |
| 7,428,816 B2 | 9/2008 | Singh et al. |
| 2003/0127115 A1 | 7/2003 | Thomas et al. |
| 2004/0089839 A1 | 5/2004 | Thomas et al. |
| 2005/0107246 A1 | 5/2005 | Thomas et al. |
| 2006/0266976 A1 | 11/2006 | Minor et al. |
| 2009/0272134 A1 * | 11/2009 | Hulse et al. ................. 62/112 |
| 2010/0326095 A1 * | 12/2010 | Van Horn et al. ............ 62/77 |
| 2011/0240254 A1 | 10/2011 | Rached et al. |

FOREIGN PATENT DOCUMENTS

| | | |
|---|---|---|
| WO | 2009/089511 A2 | 7/2009 |
| WO | 2010/061084 A1 | 6/2010 |
| WO | 2011/015738 A1 | 2/2011 |

OTHER PUBLICATIONS

PCT Search Report, PCT/US09/66828, dated Feb. 4, 2010.

* cited by examiner

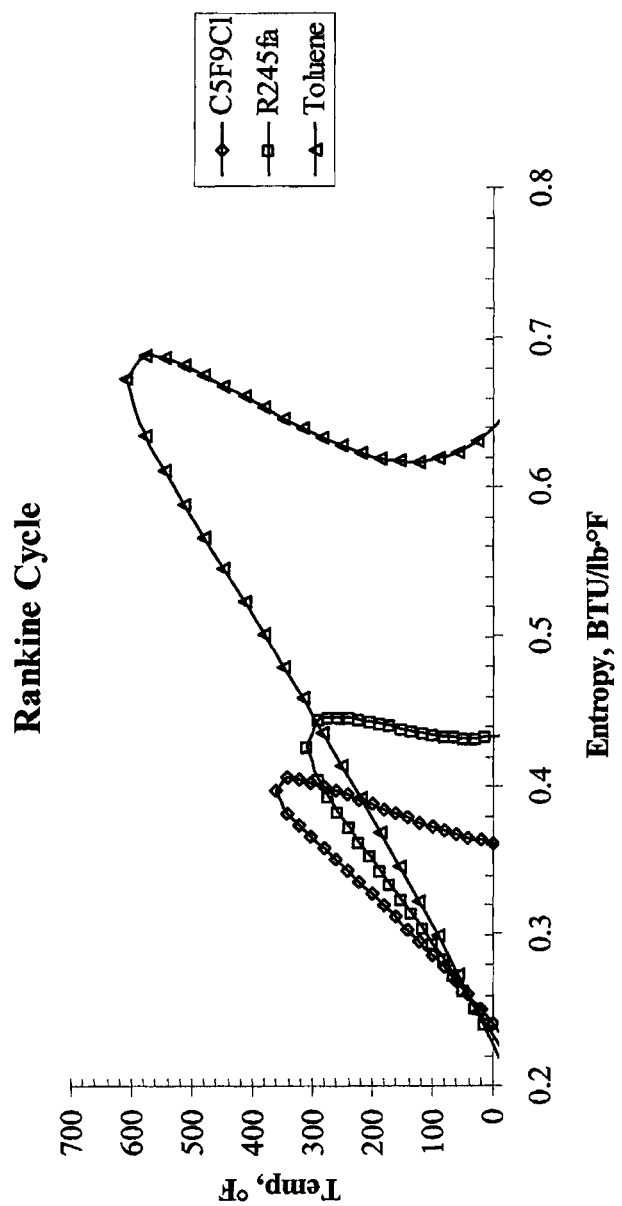

CHLORO- AND BROMO-FLUORO OLEFIN COMPOUNDS USEFUL AS ORGANIC RANKINE CYCLE WORKING FLUIDS

REFERENCE TO RELATED APPLICATIONS

This application claims the priority benefit of U.S. Provisional Application No. 61/120,125 filed Dec. 5, 2008, which is incorporated herein by reference. This application also claims the priority benefit and is a continuation in part of U.S. patent application Ser. No. 12/351,807 (pending), filed Jan. 9, 2009, which is also incorporated herein by reference.

BACKGROUND 1.0 Field of Invention

The present invention generally relates to organic Rankine cycle working fluids. More particularly, the invention relates to chloro- and bromo-fluoro-olefins as organic Rankine cycle working fluids.

2.0 Description of Related Art

Water, usually in the form of steam, is by far the most commonly employed working fluid used to convert thermal energy into mechanical energy. This is, in part, due to its wide availability, low cost, thermal stability, nontoxic nature, and wide potential working range. However, other fluids such as ammonia have been utilized in certain applications, such as in Ocean Thermal Energy Conversion (OTEC) systems. In some instances, fluids such as CFC-113 have been utilized to recover energy from waste heat, such as exhausts from gas turbines. Another possibility employs two working fluids, such as water for a high temperature/pressure first stage and a more volatile fluid for a cooler second stage. These hybrid power systems (also commonly referred to as binary power systems) can be more efficient than employing only water and/or steam.

To achieve a secure and reliable power source, data centers, military installations, government buildings, and hotels, for example, use distributed power generation systems. To avoid loss of service that can occur with loss of grid power, including extensive cascading power outages that can occur when equipment designed to prevent such an occurrence fails, the use of distributed power generation is likely to grow. Typically, an on-site prime mover, such as a gas microturbine, drives an electric generator and manufactures electricity for on-site use. The system is connected to the grid or can run independent of the grid in some circumstances. Similarly, internal combustion engines capable of running on different fuel sources are used in distributed power generation. Fuel cells are also being commercialized for distributed power generation. Waste heat from these sources as well as waste heat from industrial operations, landfill flares, and heat from solar and geothermal sources can be used for thermal energy conversion. For cases where low- to medium-grade thermal energy is available, typically, an organic working fluid is used in a Rankine cycle (instead of water). The use of an organic working fluid is largely due to the high volumes (large equipment sizes) that would need to be accommodated if water were used as the working fluid at these low temperatures.

The greater the difference between source and sink temperatures, the higher the organic Rankine cycle thermodynamic efficiency. It follows that organic Rankine cycle system efficiency is influenced by the ability to match a working fluid to the source temperature. The closer the evaporating temperature of the working fluid is to the source temperature, the higher the efficiency will be. The higher the working fluid critical temperature, the higher the efficiency that can be attained. However, there are also practical considerations for thermal stability, flammability, and materials compatibility that bear on the selection of a working fluid. For instance, to access high temperature waste heat sources, toluene is often used as a working fluid. However, toluene is flammable and has toxicological concerns. In the temperature range of 175° F. to 500° F. (79° C. to 260° C.), non-flammable fluids such as HCFC-123 (1,1-dichloro-2,2,2-trifluoroethane) and HFC-245fa (1,1,1,3,3-pentafluoropropane) are used. However, HCFC-123 has a relatively low permissible exposure level and is known to form toxic HCFC-133a at temperatures below 300° F. To avoid thermal decomposition, HCFC-123 may be limited to an evaporating temperature of 200° F.-250° F. (93° C.-121° C.). This limits the cycle efficiency and work output. In the case of HFC-245fa, the critical temperature is lower than optimum. Unless more robust equipment is used to employ a trans-critical cycle, the HFC-245fa organic Rankine cycle is held below the 309° F. (154° C.) critical temperature. To increase the useful work output and/or efficiency of an organic Rankine cycle beyond the limitations noted above for HCFC-123 and HFC-245fa, it becomes necessary to find working fluids with higher critical temperatures so that available source temperatures such as gas turbine and internal combustion engine exhaust can be approached more closely.

Certain members of a class of chemicals known as HFCs (hydrofluorocarbons) have been investigated as substitutes for compounds known as CFCs (chlorofluorocarbons) and HCFCs (hydrochlorofluorocarbons). Yet both CFCs and HCFCs have been shown to be deleterious to the planet's atmospheric ozone layer. The initial thrust of the HFC development was to produce nonflammable, non-toxic, stable compounds that could be used in air conditioning/heat pump/insulating applications. However, few of these HFCs have boiling points much above room temperature. As mentioned above, working fluids with critical temperatures higher than, for example, HFC-245fa, are desirable. Since boiling point parallels critical temperature, it follows that fluids with higher boiling points than HFC-245fa are desired.

A feature of certain hydrofluoropropanes, including HFC-245fa as compared to fluoroethanes and fluoromethanes, is a higher heat capacity due, in part, to an increase in the vibrational component contribution. Essentially, the longer chain length contributes to the freedom to vibrate; noting, of course, that the constituents and their relative location on the molecule also influence the vibrational component. Higher heat capacity contributes to higher cycle efficiency due to an increased work extraction component and also an increase in overall system efficiency due to improved thermal energy utilization (higher percentage of the available thermal energy is accessed in sensible heating). Moreover, the smaller the ratio of latent heat of vaporization to heat capacity, the less likely there will be any significant pinch point effects in heat exchanger performance. Hence, in comparison to HFC-245fa and HCFC-123, working fluids that possess, for example, higher vapor heat capacity, higher liquid heat capacity, lower latent heat-to-heat capacity ratio, higher critical temperature, and higher thermal stability, lower ozone depletion potential, lower global warming potential, non-flammability, and/or desirable toxicological properties would represent improvements over fluids such as HFC-245fa and HCFC-123.

Industry is continually seeking new fluorocarbon based working fluids which offer alternatives for refrigeration, heat pump, foam blowing agent and energy generation applications. Currently, of particular interest, are fluorocarbon-based compounds which are considered to be environmentally safe substitutes for fully and partially halogenated fluorocarbons (CFCs and HCFCs) such as trichlorofluoromethane (CFC- 11), 1,1-dichloro-1-fluoroethane (HCFC-141b) and 1,1-dichloro-2,2-trifluoroethane (HCFC-123) which are regulated in connection with the need to conserve the earth's protective ozone layer. Similarly, fluids that have a low global warming potential (affecting global warming via direct emissions) or low life cycle climate change potential (LCCP), a system view of global warming impact, are desirable. In the latter case, organic Rankine cycle improves the LCCP of many fossil fuel driven power generation systems. With improved overall thermal efficiency, these systems that incorporate organic Rankine cycle can gain additional work or electric power output to meet growing demand without consuming additional fossil fuel and without generating additional carbon dioxide emissions. For a fixed electric power demand, a smaller primary generating system with the organic Rankine cycle system incorporated can be used. Here, too, the fossil fuel consumed and subsequent carbon dioxide emissions will be less compared to a primary system sized to supply the same fixed electric power demand. The substitute materials should also possess chemical stability, thermal stability, low toxicity, non-flammability, and efficiency in-use, while at the same time not posing a risk to the planet's atmosphere. Furthermore, the ideal substitute should not require major engineering changes to conventional technology currently used. It should also be compatible with commonly used and/or available materials of construction.

Rankine cycle systems are known to be a simple and reliable means to convert heat energy into mechanical shaft power. Organic working fluids are useful in place of water/steam when low-grade thermal energy is encountered. Water/steam systems operating with low-grade thermal energy (typically 400° F. and lower) will have associated high volumes and low pressures. To keep system size small and efficiency high, organic working fluids with boiling points near room temperature are employed. Such fluids have higher gas densities lending to higher capacity and favorable transport and heat transfer properties lending to higher efficiency as compared to water at low operating temperatures.

In industrial settings, there are more opportunities to use flammable working fluids such as toluene and pentane, particularly when the industrial setting has large quantities of flammables already on site in processes or storage. For instances where the risk associated with use of a flammable working fluid is not acceptable, such as power generation in populous areas or near buildings, non-flammable fluorocarbon fluids such as CFC-11, CFC-113 and HCFC-123 are used. Although these materials are non-flammable, they were a risk to the environment because of their ozone-depletion potential.

Ideally, the organic working fluid should be environmentally acceptable, that is, have little or no ozone depletion potential and low global warming potential, non-flammable, of a low order of toxicity, and operate at positive pressures. More recently, hydrofluorocarbons such as HFC-245fa, HFC-365mfc, and HFC-43-10mee have been employed as organic Rankine cycle working fluids either neat or in mixtures with other compounds. With regard to global warming potential of working fluids, existing fluids based on hydrofluorocarbons such as HFC-245fa, HFC-356mfc, HFC-43-10, hydrofluoroethers such as commercially available HFE-7100 (3M) have global warming potentials that may be considered unacceptably high in light of a given countries environmental circumstances and subsequent regulatory policies.

Organic Rankine cycle systems are often used to recover waste heat from industrial processes. In combined heat and power (cogeneration) applications, waste heat from combustion of fuel used to drive the prime mover of a generator set is recovered and used to make hot water for building heat, for example, or for supplying heat to operate an absorption chiller to provide cooling. In some cases, the demand for hot water is small or does not exist. The most difficult case is when the thermal requirement is variable and load matching becomes difficult, confounding efficient operation of the combined heat and power system. In such an instance, it is more useful to convert the waste heat to shaft power by using an organic Rankine cycle system. The shaft power can be used to operate pumps, for example, or it may be used to generate electricity. By using this approach, the overall system efficiency is higher and fuel utilization is greater. Air emissions from fuel combustion can be decreased since more electric power can be generated for the same amount of fuel input.

SUMMARY OF THE INVENTION

Aspects of the present invention are directed to processes of using working fluids comprising compounds having the structure of formula (I):

wherein $R_1$, $R_2$, $R_3$, and $R_4$ are each independently selected from the group consisting of: H, F, Cl, Br, and $C_1$-$C_6$ alkyl, at least $C_6$ aryl, at least $C_3$ cycloalkyl, and $C_6$-$C_{15}$ alkylaryl optionally substituted with at least one F, Cl, or Br, wherein formula (I) contains at least one F and at least one Cl or Br. Preferably, the compounds that are brominated have no hydrogen (i.e., are fully halogenated). In a particularly preferred embodiment, the compound is a monobromopentafluoropropene, preferably $CF_3CBr\!=\!CF_2$. In other preferred embodiments, the working fluids comprise $C_3F_3H_2Cl$ (particularly 1-chloro-3,3,3-trifluoropropene 1233zd(Z) and/or 1233zd(E)), $CF_3CF\!=\!CFCF_2CF_2Cl$ and $CF_3CCl\!=\!CFCF_2CF_3$, and mixtures thereof.

Embodiments of the invention are directed to processes for converting thermal energy to mechanical energy by vaporizing a working fluid and expanding the resulting vapor or vaporizing the working fluid and forming a pressurized vapor of the working fluid. Further embodiments are directed to a binary power cycle and a Rankine cycle system having a secondary loop.

BRIEF DESCRIPTION OF THE DRAWINGS

FIG. 1 depicts a graph of temperature-diagrams of working fluids in a Rankine Cycle.

DETAILED DESCRIPTION OF THE INVENTION

The present invention is directed to processes using working fluids comprising compounds having the structure of formula (I):

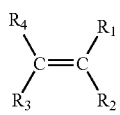

(I)

wherein $R_1$, $R_2$, $R_3$, and $R_4$ are each independently selected from the group consisting of: H, F, Cl, Br, and $C_1$-$C_6$ alkyl, at least $C_6$ aryl, in particular $C_6$-$C_{15}$ aryl, at least $C_3$ cycloalkyl, in particular $C_6$-$C_{12}$ cycloalkyl, and $C_6$-$C_{15}$ alkylaryl, optionally substituted with at least one F, Cl, or Br, wherein formula (I) contains at least one F and at least one Cl or one Br. Preferably, the compounds that are brominated have no hydrogen (i.e., are fully halogenated). In a particularly preferred embodiment, the compound is a monobromopentafluoropropene, preferably $CF_3CBr=CF_2$. In other preferred embodiments, the working fluids comprise $C_3F_3H_2Cl$ (particularly 1-chloro-3,3,3-trifluoropropene 1233zd(Z) and/or 1233zd(E)), $CF_3CF=CFCF_2CF_2Cl$ and $CF_3CCl=CFCF_2CF_3$, and mixtures thereof.

Suitable alkyls include, but are not limited to, methyl, ethyl, and propyl. Suitable aryls include, but are not limited to phenyl. Suitable alkylaryl include, but are not limited to methyl, ethyl, or propyl phenyl; benzyl, methyl, ethyl, or propyl benzyl, ethyl benzyl. Suitable cycloalkyls include, but are not limited to, methyl, ethyl, or propyl cyclohexyl. Typical alkyl group attached (at the ortho, para, or meta positions) to the aryl can have $C_1$-$C_7$ alkyl chain. The compounds of formula (I) are preferably linear compounds although branched compounds are not excluded.

In particular, the organic Rankine cycle system working fluids comprise compounds containing either at least one chlorine atom or bromine atom and at least one fluorine in compounds of the formula $CxFyHzCl_n$ or $CxFyHzBr_n$ wherein $y+z+n=2x$, x is at least 3, y is at least 1, z is 0 or a positive number, and n is 1 or 2. In particular, x is 3 to 12, and y is 1 to 23.

For example, in certain embodiments, the working fluids comprise compounds from the group $C_3F_3H_2Cl$ (hydrochlorofluoroolefin 1233zd(Z) and hydrochlorofluoroolefin 1233zd(E)), monobromopentafluoropropenes, particularly $CF_3CBr=CF_2$ (1215-Br), $CF_3CF=CFCF_2CF_2Cl$ and $CF_3CCl=CFCF_2CF_3$, and mixtures. In certain embodiments the working fluid consists essentially of 1233zd(Z). In certain other embodiments, the working fluid consists essentially of 1233zd(E).

The working fluids of the present invention have an entropy/temperature relationship at saturated vapor conditions that allows their use in heat to mechanical conversions. The fluids of the present invention either have a saturation curve that parallels isentropic expansion, which is very desirable, or the fluids of the invention have a saturation curve with a positive slope meaning superheated vapor will exit the expander and thus be candidate for further improvement of efficiency by use of a recuperator. These latter fluids are also desirable but systems requiring a recuperator have a higher material cost and are thus more expensive. Fluids that have a negative slope to the saturation curve are least desirable in that there is a risk of working fluid condensation during expansion sometimes referred to as wet expansion. The fluids of the present invention do not display this wet expansion behavior.

Heat energy can be converted to mechanical energy in a Rankine cycle in a process known as isentropic expansion. For example, as the gas at a higher temperature and pressure is expanded through a turbine to a region of lower pressure, it does work upon the turbine, exiting the turbine at a lower pressure and temperature. The difference in the enthalpies of the gas between the two points is equal to the amount of work that the gas does on the turbine. If the higher temperature, higher pressure gas has a decrease in its entropy as the temperature and pressure is lowered, the gas will not condense in an isentropic expansion; in other words, it will not partially liquefy as it drops in temperature and pressure across the turbine. Such condensation can cause unwanted wear and tear on the mechanical device (turbine, in this case), and can only be overcome by superheating the vapor prior to its entering the turbine. For small molecular species such as water, ammonia and dichlorodifluoromethane, superheating of the vapor is required to prevent significant condensation during an isentropic expansion. However, for larger molecules such as HCFC-123, HFC-245fa, and the compounds of this invention, the entropy increases as the temperature is raised (in a saturated vapor), and condensation will not occur in an isentropic expansion.

As mentioned in the background, with regard to global warming potential of working fluids, existing fluids based on hydrofluorocarbons such as HFC-245fa, HFC-356mfc, HFC-43-10, hydrofluoroethers such as commercially available HFE-7100 (3M) have global warming potentials that may be considered unacceptably high in light of current environmental circumstances and various regulatory policies.

In such cases, the fluids of the invention, having notably lower global warming potential may be used as the working fluids or as components of working fluid mixtures. In this way, viable mixtures of, for example, the aforementioned HFCs with at least one compound of the invention can be used as organic Rankine cycle fluids, having the benefit of reduced global warming potential while preserving an acceptable level of performance.

The working fluids of the invention are useful as energy conversion fluids. Such compounds meet the requirement for not adversely affecting atmospheric chemistry and would be a negligible contributor to ozone depletion and to greenhouse global warming in comparison to fully and partially halogenated hydrocarbons and are suitable for use as working fluids for use in thermal energy conversion systems.

Thus, in a method for converting thermal energy to mechanical energy, particularly using an organic Rankine cycle system, working fluids of the invention comprise at least one compound having the structure of formula (I) as defined above.

Mathematical models have substantiated that such compounds and mixtures thereof, will not adversely affect atmospheric chemistry, being a negligible contributor to ozone depletion and to green-house global warming in comparison to the fully and partially halogenated saturated hydrocarbons.

The present invention meets the need in the art for a working fluid which has low ozone depletion potential and is a negligible contributor to green-house global warming compared with fully halogenated CFC and partially halogenated HCFC materials, is effectively nonflammable, and is chemically and thermally stable in conditions where it is likely to be employed. That is, the materials are not degraded by chemical reagents for example, acids, bases, oxidizing agent and the like or by higher temperature more than ambient (25° C.). These materials have the proper boiling points and thermodynamic characteristics that would be usable in thermal energy conversion to mechanical shaft power and electric power generation; they could take advantage of some of the latent heat contained in low pressure steam that is presently not well utilized.

The above listed materials may be employed to extract additional mechanical energy from low grade thermal energy sources such as industrial waste heat, solar energy, geothermal hot water, low-pressure geothermal steam (primary or secondary arrangements) or distributed power generation equipment utilizing fuel cells or prime movers such as turbines, microturbines, or internal combustion engines. Low-pressure steam can also be accessed in a process known as a binary Rankine cycle. Large quantities of low pressure steam can be found in numerous locations, such as in fossil fuel powered electrical generating power plants. Binary cycle processes using these working fluids would prove especially useful where a ready supply of a naturally occurring low temperature "reservoir", such as a large body of cold water, is available. The particular fluid could be tailored to suit the power plant coolant quality (its temperature), maximizing the efficiency of the binary cycle.

An embodiment of the invention comprises a process for converting thermal energy to mechanical energy in a Rankine cycle (in which the cycle is repeated) comprising the steps of vaporizing a working fluid with a hot heat source, expanding the resulting vapor and then cooling with a cold heat source to condense the vapor, and pumping the condensed working fluid, wherein the working fluid is at least one compound having the structure of formula (I) as defined above. The temperatures depend on the vaporization temperature and condensing temperature of the working fluid Another embodiment of the invention comprises a process for converting thermal energy to mechanical energy which comprises heating a working fluid to a temperature sufficient to vaporize the working fluid and form a pressurized vapor of the working fluid and then causing the pressurized vapor of the working fluid to perform mechanical work, wherein the working fluid is at least one compound having structure of formula (I) as defined above. The temperature depends on the vaporization temperature of the working fluid.

Working fluid temperature in the boiler (evaporator) is dictated by the source temperature. Source temperatures can vary widely; 90° C. geothermal to >800° C. for combustion gases or some fuel cells. If a low boiling point fluid is used, pressures will be higher in the boiler and vice versa. The upper pressure limit is likely to be governed by cost since thicker-walled vessels, piping, and components would typically cost more. Also, as boiling point increases, so does critical temperature. Using higher boiling fluids for higher source temperatures improves cycle efficiency.

In the embodiment above, the mechanical work may be transmitted to an electrical device such as a generator to produce electrical power.

A further embodiment of the invention comprises a binary power cycle comprising a primary power cycle and a secondary power cycle, wherein a primary working fluid comprising high temperature water vapor or an organic working fluid vapor is used in the primary power cycle, and a secondary working fluid is used in the secondary power cycle to convert thermal energy to mechanical energy, wherein the secondary power cycle comprises: heating the secondary working fluid to form a pressurized vapor and causing the pressurized vapor of the second working fluid to perform mechanical work, wherein the secondary working fluid comprises at least one compound having the formula (I) as defined above. Such binary power cycles are described in, for example U.S. Pat. No. 4,760,705 hereby incorporated by reference in its entirety.

A further embodiment of the invention comprises a process for converting thermal energy to mechanical energy comprising a Rankine cycle system and a secondary loop; wherein the secondary loop comprises a thermally stable sensible heat transfer fluid interposed between a heat source and the Rankine cycle system and in fluid communication with the Rankine cycle system and the heat source to transfer heat from the heat source to the Rankine cycle system without subjecting the organic Rankine cycle system working fluid to heat source temperatures; wherein the working fluid is at least one compound having structure of formula (I) as defined above.

This process is beneficial when it is desired to address higher source temperatures without subjecting a working fluid, such as those of the invention, directly to the high source temperatures. If direct heat exchange between the working fluid and the heat source is practiced, the design must include means to avoid thermal decomposition of the working fluid, particularly if there is an interruption of flow. To avoid the risk and extra expense for the more elaborate design, a more stable fluid, such as a thermal oil, can be used to access the high-temperature source. This provides a means to address the high source heat, manage design complexity/cost, and utilize a fluid with otherwise desirable properties.

The present invention is more fully illustrated by the following non-limiting examples. It will be appreciated that variations in proportions and alternatives in elements of the components of the invention will be apparent to those skilled in the art and are within the scope of the invention.

Example 1

When ranking organic working fluids for their ability to deliver an efficient Rankine cycle, the higher the critical temperature, the more efficient the cycle that can be derived. This is because the evaporator temperatures can more closely approach higher temperature heat sources. Organic working fluids for Rankine cycle (sometimes referred to as power cycle) applications are employed when source temperatures are moderate to low in thermal quality. At high temperatures, water is a very efficient working fluid; however, at moderate to low temperatures, the thermodynamics of water no longer are favorable.

FIG. 1 shows a plot of the temperature-entropy diagrams for HFC-245fa (comparative), an isomeric mixture of $C_5F_9Cl$ compounds in accordance with the present invention, and toluene (comparative). Both HFC-245fa and toluene are used commercially as organic Rankine cycle working fluids. Based on the area swept out by the domes, it can be concluded that the Rankine cycle efficiency obtainable with the $C_5F_9Cl$ compounds of the present invention are comparable to that of HFC-245fa but that the efficiency is less than that attainable with toluene. However, toluene has toxicity and flammability concerns that may limit its use in various organic Rankine cycle applications. Hence the non-flammable halogenated working fluids of the invention provide a suitable alternative.

In addition to identifying working fluids with high critical temperatures, it is desirable to find fluids that have the potential for minimal impact on the environment since it is impossible to rule out leaks from storage, transport, and use of working fluids. The chemical structure of the $C_5F_9Cl$ isomers of the invention can be predicted to be short-lived in the atmosphere, thus affording a low global warming potential estimated to be on the order of 20-50.

The ability to produce such compounds and their usefulness in thermal energy conversion is demonstrated in the following examples.

Example 2

$CF_3CF$=$CFCF_2CF_2Cl$ and $CF_3CCl$=$CFCF_2CF_3$ were made by reacting hexafluoropropene and chlorotrifluoroethylene in the presence of antimony pentafluoride. These isomers co-distill at a boiling point range 52-53° C.

1. Reaction Scheme:

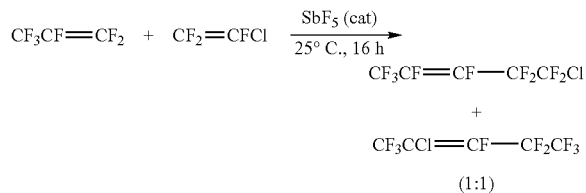

$$CF_3CF{=}CF_2 + CF_2{=}CFCl \xrightarrow[25°C., 16h]{SbF_5 \text{ (cat)}}$$
$$CF_3CF{=}CF{-}CF_2CF_2Cl$$
$$+$$
$$CF_3CCl{=}CF{-}CF_2CF_3$$
$$(1{:}1)$$

2. Procedure

To a clean, dry Parr reactor/autoclave was added SbF5 (40 g, 0.16 mol), partially evacuated and sealed. The Parr Reactor was cooled to −30 to −35° C., evacuated and $CF_3CF{=}CF_2$ (128 g, 0.85 mol) and $CF_2{=}CFCl$ (92 g, 0.78 mol) were condensed, sequentially. The reactor was then sealed, gradually brought to room temperature (~25° C.) with stirring and maintained at this temperature for 16 hours; the pressure in the reactor dropped from 80 psi to 40 psi over this period. More volatile materials including any unreacted starting compounds in the reactor was vented through a cold trap (ice+salt) (20 g product was condensed in the trap). The remaining product in the Parr Reactor was collected into a cooled (dry ice) metal cylinder by heating the Parr reactor from RT to ~50° C. reactor; a total of 125 g product was collected (yield=60% based on CTFE). Further purification was accomplished by distillation at 52-53° C./atmospheric pressure to afford isomer mixture —$CF_3CF{=}CF{-}CF_2CF_2Cl$ and $CF_3CCl{=}CF{-}CF_2CF_3$ (1:1)—as a colorless liquid (100 g).

Analytical data is consistent with the structure. GC/MS (m/e, ion); 226 for M$^+$, (M=$C_5C_1F_9$). 19F NMR (CDCl$_3$) δ=−69.1 (3F, dd, J=21 & 8 Hz), −72.1 (2F, dq, overlaps, J=6 & 5.7 Hz), −117.7 (2F, m), −155.4 (1F, dm), and −157.5 (dm) ppm for $CF_3CF{=}CF{-}CF_2CF_2Cl$; −64.3 (3F, d, J=24 Hz), −111.5 (1F, m), −118.9 (2F, m) and −83.9 (3F, dq, overlaps, J=3 Hz) ppm for $CF_3CCl{=}CF{-}CF_2CF_3$. The ratio of isomers (50:50) was determined by integration of $CF_3$ group in the 19F NMR.

Example 3

This example illustrates that the chloro-fluoro olefins of the invention, the $C_5F_9Cl$ isomers and the HCFO-1233zd isomers, are useful as organic Rankine cycle working fluids.

The effectiveness of various working fluids in an organic Rankine cycle is compared by following the procedure outlined in Smith, J. M. et al., *Introduction to Chemical Engineering Thermodynamics*; McGraw-Hill (1996). The organic Rankine cycle calculations were made using the following conditions: pump efficiency of 75%, expander efficiency of 80%, boiler temperature of 130° C., condenser temperature of 45° C. and 1000 W of heat supplied to the boiler. Performance of various refrigerants is given in Table 1. Commercially available fluids including hydrofluorocarbons such as HFC-245fa (available from Honeywell), HFC-365mfc (available from Solvay), HFC-4310mee (available from DuPont) and the hydrofluoroether HFE-7100 (available from 3M) are included in the comparison. The thermal efficiency of HCFO-1233zd (E) is the highest among all the compounds evaluated. The $C_5F_9Cl$, HCFO-1233zd(Z) and HCFO-1233zd(E) also have the added benefit of non-flammability and low global warming potential. This example demonstrates that chloro-fluoro olefins can be used in power generation through an organic Rankine cycle.

TABLE 1

| | | Cycle Results | | | | | | |
|---|---|---|---|---|---|---|---|---|
| | Units | Comp 245fa | Comp 365mfc | Comp 7100 | Comp 4310mee | Inv $C_5F_9Cl$ | Inv 1233zd(Z) | Inv 1233zd(E) |
| Condenser Press | psia | 338.7 | 146.7 | 93.6 | 114.6 | 106.0 | 116.6 | 281.4 |
| Condenser Press | psia | 42.9 | 16.7 | 8.7 | 7.6 | 10.1 | 12.6 | 36.1 |
| Superheat in Boiler | ° C. | 0.0 | 0.0 | 0.0 | 0.0 | 0.3 | 0.0 | 0.0 |
| Fluid Flow | g/s | 4.4 | 4.1 | 5.4 | 5.1 | 6.0 | 3.7 | 4.5 |
| Pump Work | J/g | 2.12 | 0.99 | 0.53 | 0.66 | 0.52 | 0.70 | 1.79 |
| Expander Work | J/g | −30.22 | −32.22 | −22.00 | −24.21 | −20.12 | −37.81 | −30.81 |
| Net Work | J/g | −28.10 | −31.23 | −21.47 | −23.54 | −19.59 | −37.11 | −29.02 |
| Net Work | W | −122.74 | −127.91 | −116.21 | −119.33 | −116.75 | −138.79 | −130.29 |
| Q Boiler | J/g | 228.94 | 244.13 | 184.78 | 197.30 | 167.83 | 267.38 | 222.75 |
| Thermal Efficiency | | 0.123 | 0.128 | 0.116 | 0.119 | 0.117 | 0.139 | 0.130 |

Example 4

In addition to the chlorofluoroolefins described above, bromofluoroolefins such as those of Table 2 cover a range of boiling points lower than the boiling point of water and are thus useful in a range of thermal energy conversion applications, that is, a range of source temperatures. The compounds with the high boiling points (>50° C.) are most likely to be used for higher waste heat sources and are comparable with toluene, for example.

TABLE 2

| Bromofluoroolefin compounds | |
|---|---|
| Compound | Boiling point, ° C. |
| CBrF=CF2 | −2 |
| CBrH=CF2 | 6 |

TABLE 2-continued

Bromofluoroolefin compounds

| Compound | Boiling point, ° C. |
|---|---|
| $CF_2$=$CBrCF_3$ | 25 |
| $CF_2$=$CFCBrF_2$ | 28 |
| $CHF$=$CBrCF_3$ | 28 |
| $CHBr$=$CFCF_3$ | 31 |
| $CH_2$=$CBrCF_3$ | 34.5 |
| $CF_2$=$CHCF_2Br$ | 35 |
| $CHBr$=$CHCF_3$ | 40 |
| $CHF$=$CHCBrF_2$ | 41.5 |
| $CH_2$=$CHCBrF_2$ | 42 |

TABLE 2-continued

Bromofluoroolefin compounds

| Compound | Boiling point, ° C. |
|---|---|
| $CH_2$=$CHCF_2CBrF_2$ | 54.5 |
| $CH_2$=$CHCBrFCF_3$ | 55.4 |
| $CBrF_2CF(CF_3)CH$=$CH_2$ | 79 |
| $CH_2$=$C(CF_3)CBrF_2$ | 79.5 |
| $CF_3CF$=$CHCH_2Br$ | 81 @ 749 Torr |
| $CH_3CH$=$CHCBrFCF_3$ | 92.6 @ 750 Torr |
| $CF_3CF$=$CHCHBrCH_3$ | 95 @ 752 Torr |
| $CH_2$=$CBrCF_2CF_2CF_3$ | 96 |
| $CH_3CH$=$CHCF_2CF_2Br$ | 97 |
| $CF_2$=$CFCH_2CH_2Br$ | 99 |

Example 5

This example illustrates that the bromo-fluoro olefins of the invention are useful as organic Rankine cycle working fluids. In particular, $CF_3CBr$=$CF_2$ is used to illustrate the usefulness if bromo-fluoro olefins in an organic Rankine cycle. Also, the efficiency of fully halogenated bromofluoropropenes is compared to non-fully halogenated bromofluoropropenes. These results show, unexpectedly, that fully halogenated bromofluoropropenes are more efficient as working fluids in organic Rankine cycles compared to non-fully halogenated bromofluoropropenes.

The effectiveness of various working fluids in an organic Rankine cycle is compared by following the procedure outlined in Smith, J. M. et al., *Introduction to Chemical Engineering Thermodynamics*; McGraw-Hill (1996). The organic Rankine cycle calculations were made using the following conditions: a pump efficiency of 75%, expander efficiency of 80%, boiler temperature of 130° C., condenser temperature of 45° C. and 1000 W of heat supplied to the boiler. Performance of various refrigerants is given in Table 3. The commercially available fluid HFC-245fa (available from Honeywell) is included in the comparison. The bromo-fluoro olefins also have the added benefit of non-flammability and low global warming potential. The bromo-fluoro olefins also have a higher thermal efficiency than commercially available fluids. This example demonstrates that bromo-fluoro olefins can be used in power generation through an organic Rankine cycle.

TABLE 3

Cycle Results

| | Units | Comp 245fa | Inv CHBr=CHCF3 | Comp CF2=CHCF2Br | Comp CHBr=CFCF3 |
|---|---|---|---|---|---|
| Condenser Press | psia | 338.7 | 161.39 | 177.01 | 179.21 |
| Condenser Press | psia | 42.9 | 18.56 | 22.67 | 23.06 |
| Superheat in Boiler | ° C. | 0 | 0 | 0 | 0 |
| Fluid Flow | g/s | 4.4 | 5.3 | 6.1 | 6.1 |
| Pump Work | J/g | 2.12 | 0.88 | 0.89 | 0.9 |
| Expander Work | J/g | −30.22 | −26.2 | −22.47 | −22.39 |
| Net Work | J/g | −28.1 | −25.32 | −21.58 | −21.49 |
| Net Work | W | −122.74 | −134.43 | −130.83 | −130.52 |
| Q Boiler | J/g | 228.94 | 188.35 | 164.97 | 164.64 |
| Thermal Efficiency | | 0.123 | 0.134 | 0.131 | 0.131 |

Example 6

It is also beneficial in some cases to incorporate at least a second fluid component into the working fluid. In addition to performance, health, safety and environmental benefits can be derived when employing a mixture of at least two fluid components. Improvement in flammability characteristics (non-flammability), decrease in potential environmental impact, and/or decrease in occupational exposure levels due to decreased toxicity can be achieved by utilizing mixtures. For example, addition of a low global warming potential fluid to a fluid having desirable performance but a higher global warming potential can result in a fluid mixture with improved or acceptable performance, depending on the low global warming fluid's performance, and improved global warming potential as compared to the higher global warming fluid component alone. Thus it is also an objective to identify mixtures that can improve at least one characteristic of a pure fluid such as performance (such as capacity or efficiency), flammability characteristics, toxicity, or environmental impact. The compounds of the invention can be mixed with one another (other hydrochlorofluoroolefins) or with compounds such as hydrofluorocarbons, bromofluoroolefins, fluorinated ketones, hydrofluoroethers, hydrofluoroolefins, hydrofluoroolefin ethers, hydrochlorofluoroolefin ethers, hydrocarbons, or ethers.

In accordance with the conditions given in Example 3, HCFO-1223zd(Z) was added to HFC-245fa resulting in a mixture of 50% HFC-245fa (1,1,1,3,3-pentafluoropropane) and 50% HCFO-1233zd(Z) yielding a theoretical cycle efficiency of 0.128. The theoretical cycle efficiency for HFC- 245fa is 0.123. Hence, there is a 4% increase in the theoretical cycle efficiency of the mixture compared to HFC-245fa alone. The global warming potential of the mixture is 480 while that of HFC-245fa alone is 950. There is a 49% reduction in global warming potential for the mixture as compared to HFC-245fa alone. At these conditions, the evaporating pressure for the mixture (230 psia) is lower than that of HFC-245fa alone (339 psia). The equipment would operate with a lower evaporator pressure and thus have a greater difference from the maximum allowable working pressure of the equipment. This means that higher source temperatures can be accessed using the same equipment, thus improving overall thermal efficiency without necessarily exceeding the maximum allowable working pressure of the equipment.

Other mixtures are shown in the Table below

| Components | Benefit vs. without compound of the invention |
|---|---|
| 245fa/1233zd | Lower GWP, higher thermal efficiency, |
| 365mfc/1233zd | Lower GWP, higher thermal efficiency, non-flammable, |
| 365mfc/HT55 perfluoropolyether/1233zd | Lower GWP, higher thermal efficiency |
| HFE-7100 ($C_5H_3F_9O$)/1233zd | Lower GWP, higher thermal efficiency, |
| Novec 1230 ($C_6F_{10}O$)/1233zd | Improved toxicity (higher TLV-TWA) |
| HFC 43-10mee ($C_5H_2F_{10}$)/1233zd | Lower GWP, higher thermal efficiency, |
| 245fa/$C_5F_9Cl$ | Lower GWP |
| 365mfc/$C_5F_9Cl$ | Lower GWP |
| 365mfc/HT55/$C_5F_9Cl$ | Lower GWP |
| HFE-7100 ($C_5H_3F_9O$)/$C_5F_9Cl$ | Lower GWP, comparable thermal efficiency |
| Novec 1230/$C_5F_9Cl$ | |
| HFC 43-10mee ($C_5H_2F_{10}$)/$C_5F_9Cl$ | Lower GWP, comparable thermal efficiency |

Hydrofluoroether HFE-7100 and fluorinated ketone Novec® 1230 are commercially available from 3M. Hydrofluorocarbon HFC 43-10mee is commercially available from DuPont. HFC-365mfc/HT55 is commercially available from SolvaySolexis as Solkatherm® SES36. Galden® HT55 is a perfluoropolyether available from SolvaySolexis Example 7

The following provides information regarding safety and toxicity of HCFC-1233zd.
1233zd Toxicity
An Ames assay was conducted with HFO-1233zd. The study exposed bacterial cells TA 1535, TA1537, TA 98, TA 100 and WP2 uvrA both in the presence and with out S-9 metabolic activation. Exposure levels of up to 90.4% were used. The study was designed to be fully compliant with Japanese, E.U. and U.S. guidelines. Under the conditions of this study, HFO-1233zd did not induce mutations in any culture either in the presence or absence of S-9 metabolic activation.
Cardiac Sensitization
In this study a group of 6 beagle dogs were exposed to levels of 25,000, 35,000 and 50,000 ppm (only 2 dogs at this level) of HCFC-1233zd. A total of three exposures were conducted, with at least a 2-day separation between exposures. The dogs were then exposed to the test compound and given a series of injections of adrenalin of increasing dose (2 μg/kg, 4 μg/kg, 6 μg/kg and 8 μg/kg) with a minimum separation between each injection of 3 minutes, for a total of up to 12 minutes, while being exposed to the test article. It was concluded that there was no evidence or cardiac sensitization at 25,000 ppm.
LC-50 (Rat)
Rat LC-50 was determined to be 11 Vol %. This level is better than the chlorinated products, HCFC-141b and CFC-113 (about 6 vol %), and is similar to that of CFC-11.
Flammability
1233zd was evaluated for flammability per ASTM E-681 at 100° C. There were no limits of flammability.
Stability
1233zd stability was studied by subjecting the fluid to 150° C. for two weeks in the presence of coupled metal coupons (copper, aluminum, and steel) per ASHRAE 97 sealed tube test method. No significant decomposition was evident; i.e., there was no notable discoloration of the fluid and no signs of corrosion on the metal coupons.

Example 8

This example illustrates the performance of one embodiment of the present invention in which a refrigerant composition comprises HFO-1234 wherein a large proportion, and preferably at least about 75% by weight and even more preferably at least about 90% by weight, of the HFO-1234 is HFO-1234ye ($CHF_2$—CF=CHF, cis- and trans-isomers). More particularly, this example is illustrative of such a composition being used as a working fluid in a refrigerant system, High Temperature Heat Pump and Organic Rankine Cycle system. An example of the first system is one having an Evaporation Temperature of about of 35° F. and a Condensing Temperature of about 150° F. For the purposes of convenience, such heat transfer systems, that is, systems having an evaporator temperature of from about 35° F. to about 50° F. and a CT of from about 80° F. to about 120° F., are referred to herein as "chiller" or "chiller AC" systems. The operation of each of such systems using R-123 for the purposes of comparison and a refrigeration composition of the present invention comprising at least about 90% by weight of HFO-1234ye is reported in Table 12 below:

| Chiller Temp Conditions 40° F. ET and 95° F. CT | | | |
|---|---|---|---|
| Performance Property Capacity | R-123 | Trans-HFO-1234yf | Cis-HFO-1234ye |
| Rel to R-123 | 100 | 120% | 105% |
| COP Rel to R-123 | 100 | 98% | 105% |

As can be seen from the Table above, many of the important refrigeration system performance parameters are relatively close to the parameters for R-123. Since many existing refrigeration systems have been designed for R-123, or for other refrigerants with properties similar to R-123, those skilled in the art will appreciate the substantial advantage of a low GWP and/or a low ozone depleting refrigerant that can be used as replacement for R-123 or like high boiling refrigerants with relatively minimal modifications to the system. It is contemplated that in certain embodiments the present invention provides retrofitting methods which comprise replacing the refrigerant in an existing system with a composition of the present invention, preferably a composition comprising at least about 90% by weight and/or consists essentially of HFO-1234 and even more preferably any one or more of cis-HFO-1234ye, trans-HFO-1234ye, and all combinations and proportions thereof, without substantial modification of the design.

Example 9

This example illustrates the performance of one embodiment of the present invention in which a refrigerant composition comprises HFCO-1233 wherein a large proportion, and preferably at least about 75% by weight and even more preferably at least about 90% by weight, of the HFCO-1233zd is HFCO-1233zd ($CF_3$—CH=CHCl, cis- and trans-isomers). More particularly, this example illustrates the use of such a composition as a heat transfer fluid in a refrigerant system, High Temperature Heat Pump or an Organic Rankine Cycle system. An example of the first system is one having an Evaporation Temperature of about of 35° F. and a Condensing Temperature of about 150° F. For the purposes of convenience, such heat transfer systems, that is, systems having an evaporator temperature of from about 35° F. to about 50° F. and a CT of from about 80° F. to about 120° F., are referred to herein as "chiller" or "chiller AC" systems The operation of each of such systems using R-123 and a refrigeration composition comprising at least about 90% by weight of HFO-1233zd is reported in Table 13 below:

| Chiller Temp Conditions 40° F. ET and 95° F. CT | | | | |
|---|---|---|---|---|
| Performance Property Capacity | Units | R-123 | Trans HFO-1233zd | Cis-HFO-1233zd |
| Rel to R-123 COP | % | 100 | 115% | 95% |
| Rel to R-123 | % | 100 | 98% | 105% |

As can be seen from the Table above, many of the important refrigeration system performance parameters are relatively close to the parameters for R-123. Since many existing refrigeration systems have been designed for R-123, or for other refrigerants with properties similar to R-123, those skilled in the art will appreciate the substantial advantage of a low GWP and/or a low ozone depleting refrigerant that can be used as replacement for R-123 or like high boiling refrigerants with relatively minimal modifications to the system. It is contemplated that in certain embodiments the present invention provided retrofitting methods which comprise replacing the refrigerant in an existing system with a composition of the present invention, preferably a composition comprising at least about 90% by weight and/or consists essentially of HFO-1233 and even more preferably any one or more of cis-HFO-1233zd, trans-HFO-1233zd, and combinations of these in all proportions, without substantial modification of the design.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

We claim:

1. A process for converting thermal energy to mechanical energy in a Rankine cycle comprising:
vaporizing a working fluid with a low grade thermal energy heat source;
expanding the resulting vapor and then cooling with a cold heat source to condense the vapor; and
pumping the condensed working fluid;
wherein the working fluid comprises at least one compound having the formula (I):

wherein $R_1$, $R_2$, $R_3$, and $R_4$ are each independently selected from the group consisting of: H, F, Cl, Br, and $C_1$-$C_6$ alkyl, at least $C_6$ aryl, at least $C_3$ cycloalkyl, and $C_6$-$C_{15}$ alkylaryl optionally substituted with at least one F, Cl, or Br, wherein formula (I) contains at least one F and at least one Cl or Br, provided that if formula (I) contains Br, then it also contains no hydrogen and wherein at least one of $R_1$, $R_2$, $R_3$, and $R_4$ is methyl, ethyl, or propyl, optionally substituted with at least one F, Cl, or Br.

2. The process of claim 1 wherein the compound comprises $C_3F_3H_2Cl$.

3. The process of claim 1 wherein the working fluid is selected from the group consisting of 1-chloro-3,3,3-trifluoropropene (Z), 1-chloro-3,3,3-trifluoropropene (E), and combinations thereof.

4. A process for converting thermal energy to mechanical energy comprising:
heating a working fluid with a low grade thermal energy heat source to a temperature sufficient to vaporize the working fluid and form a pressurized vapor of the working fluid; and
causing the pressurized vapor of the working fluid to perform mechanical work;
wherein the working fluid comprises at least one compound having the formula (I):

wherein $R_1$, $R_2$, $R_3$, and $R_4$ are each independently selected from the group consisting of: H, F, Cl, Br, and $C_1$-$C_6$ alkyl, at least $C_6$ aryl, at least $C_3$ cycloalkyl, and $C_6$-$C_{15}$ alkylaryl optionally substituted with at least one F, Cl, or Br, wherein formula (I) contains at least one F and at least one Cl or Br, provided that if formula (I) contains Br, then it also contains no hydrogen and wherein at least one of $R_1$, $R_2$, $R_3$, and $R_4$ is methyl, ethyl, or propyl, optionally substituted with at least one F, Cl, or Br.

5. The process of claim 4 further comprising transmitting the mechanical work to an electrical device.

6. The process of claim 5 wherein the electrical device is a generator to produce electrical power.

7. A process for a binary power cycle comprising a primary power cycle and a secondary power cycle, wherein a primary working fluid comprising high temperature water vapor or an organic working fluid vapor is used in the primary power cycle, and a secondary working fluid is used in the secondary power cycle to convert thermal energy to mechanical energy wherein the secondary power cycle comprises:

heating the secondary working fluid using a low grade thermal energy source to form a pressurized vapor and causing the pressurized vapor of the secondary working fluid to perform mechanical work, wherein the secondary working fluid comprises at least one compound having the formula (I):

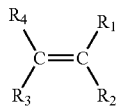

(I)

wherein $R_1$, $R_2$, $R_3$, and $R_4$ are each independently selected from the group consisting of: H, F, Cl, Br, and $C_1$-$C_6$ alkyl, at least $C_6$ aryl, at least $C_3$ cycloalkyl, and $C_6$-$C_{15}$ alkylaryl optionally substituted with at least one F, Cl, or Br, wherein formula (I) contains at least one F and at least one Cl or Br, provided that if formula (I) contains Br, then it also contains no hydrogen and wherein at least one of $R_1$, $R_2$, $R_3$, and $R_4$ is methyl, ethyl, or propyl, optionally substituted with at least one F, Cl, or Br.

8. A process for converting thermal energy to mechanical energy comprising a Rankine cycle system and a secondary loop; wherein the secondary loop comprises a thermally stable sensible heat transfer fluid interposed between a low grade thermal energy heat source and the Rankine cycle system and in fluid communication with the Rankine cycle system and the low grade thermal energy heat source to transfer heat from the heat source to the Rankine cycle system without subjecting a working fluid of the organic Rankine cycle system to heat source temperatures;

wherein the Rankine cycle system working fluid comprises at least one compound having the formula (I):

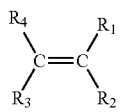

(I)

wherein $R_1$, $R_2$, $R_3$, and $R_4$ are each independently selected from the group consisting of: H, F, Cl, Br, and $C_1$-$C_6$ alkyl, at least $C_6$ aryl, at least $C_3$ cycloalkyl, and $C_6$-$C_{15}$ alkylaryl optionally substituted with at least one F, Cl, or Br, wherein formula (I) contains at least one F and at least one Cl or Br, provided that if formula (I) contains Br, then it also contains no hydrogen and wherein at least one of $R_1$, $R_2$, $R_3$, and $R_4$ is methyl, ethyl, or propyl, optionally substituted with at least one F, Cl, or Br.

9. An organic Rankine cycle working fluid for a low grade thermal energy heat source comprising at least one compound having the formula (I):

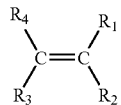

(I)

wherein $R_1$, $R_2$, $R_3$, and $R_4$ are each independently selected from the group consisting of: H, F, Cl, Br, and $C_1$-$C_6$ alkyl, at least $C_6$ aryl, at least $C_3$ cycloalkyl, and $C_6$-$C_{15}$ alkylaryl optionally substituted with at least one F, Cl, or Br, wherein formula (I) contains at least one F and at least one Cl or Br, provided that if formula (I) contains Br, then it also contains no hydrogen and wherein at least one of $R_1$, $R_2$, $R_3$, and $R_4$ is methyl, ethyl, or propyl, optionally substituted with at least one F, Cl, or Br.

10. The working fluid of claim 9 wherein the compound comprises $C_3F_3H_2Cl$.

11. The working fluid of claim 9 wherein the compound is selected from the group consisting of 1-chloro-3,3,3-trifluoropropene (Z), 1-chloro-3,3,3-trifluoropropene (E), and combinations thereof.

12. The working fluid of claim 11 wherein said working fluid consists essentially of 1-chloro-3,3,3-trifluoropropene (Z), 1-chloro-3,3,3-trifluoropropene (E), and combinations thereof.

13. The working fluid of claim 11 wherein said working fluid consists essentially of 1-chloro-3,3,3-trifluoropropene (Z).

14. The process of claim 1, wherein said working fluid has a thermal efficiency of at least 0.13 in the Rankine cycle.

15. The process of claim 1, wherein said working fluid consists essentially of 1-chloro-3,3,3-trifluoropropene (E).

16. The process of claim 4, wherein said working fluid consists essentially of 1-chloro-3,3,3-trifluoropropene (E).

17. The process of claim 7, wherein said working fluid consists essentially of 1-chloro-3,3,3-trifluoropropene (E).

18. The process of claim 8, wherein said working fluid consists essentially of 1-chloro-3,3,3-trifluoropropene (E).

19. The working fluid of claim 9, wherein said working fluid consists essentially of 1-chloro-3,3,3-trifluoropropene (E).

* * * * *